(12) United States Patent
Cully et al.

(10) Patent No.: US 9,931,193 B2
(45) Date of Patent: Apr. 3, 2018

(54) ELASTIC STENT GRAFT

(71) Applicant: W. L. Gore & Associates, Inc., Newark, DE (US)

(72) Inventors: Edward H Cully, Flagstaff, AZ (US); Jeffrey B Duncan, Flagstaff, AZ (US); Ryan D Kariniemi, Flagstaff, AZ (US); Thomas E Kariniemi, Flagstaff, AZ (US); Jeffrey J Kustusch, Flagstaff, AZ (US); Jared S Nelson, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 814 days.

(21) Appl. No.: 13/755,481

(22) Filed: Jan. 31, 2013

(65) Prior Publication Data

US 2014/0135897 A1 May 15, 2014

Related U.S. Application Data

(63) Continuation-in-part of application No. 13/675,764, filed on Nov. 13, 2012, now abandoned.

(51) Int. Cl.
*A61F 2/07* (2013.01)
*A61L 31/04* (2006.01)

(52) U.S. Cl.
CPC .............. *A61F 2/07* (2013.01); *A61L 31/048* (2013.01); *A61F 2002/072* (2013.01)

(58) Field of Classification Search
CPC ...... A61F 2/07; A61F 2002/072; A61L 27/34; A61L 27/28; A61L 27/16; A61L 27/507
See application file for complete search history.

(56) References Cited

U.S. PATENT DOCUMENTS

| | | | |
|---|---|---|---|
| 3,953,566 A | 4/1976 | Gore | |
| 4,187,390 A | 2/1980 | Gore | |
| | (Continued) | | |

FOREIGN PATENT DOCUMENTS

| | | |
|---|---|---|
| EP | 0 293 090 | 11/1988 |
| EP | 0313263 A2 | 4/1989 |
| | (Continued) | |

OTHER PUBLICATIONS

Partial International Search Report for PCT/US2012/065066, dated Jul. 1, 2013, corresponding to U.S. Appl. No. 13/675,959, 3 pages.
(Continued)

*Primary Examiner* — Thomas McEvoy

(57) ABSTRACT

A stent graft including (1) a stent having a wall having at least one opening, an outer surface, and an inner surface and (2) a covering of a composite material having a least one expanded fluoropolymer membrane and an elastomer is provided. The cover can be used to cover the outer and/or the inner surface of the stent. The expanded fluoropolymer membrane contains serpentine fibrils. In exemplary embodiments, the fluoropolymer is polytetrafluoroethylene. The composite material may be axially and/or circumferentially wrapped around the stent. The composite material is fold-free throughout its operating diameter range and exhibits a sharp increase in stiffness at a predetermined diameter. The stent graft can be designed to have a stop point in either a radial or axial direction. The stent graft can advantageously be implanted undersized with respect to a nominal diameter without having material infolding.

24 Claims, 8 Drawing Sheets

(56) References Cited

U.S. PATENT DOCUMENTS

| | | | |
|---|---|---|---|
| 4,877,661 A * | 10/1989 | House | B29C 55/005 264/288.8 |
| 4,955,899 A | 9/1990 | Della Corna et al. | |
| 5,026,513 A | 6/1991 | House et al. | |
| 5,071,609 A | 12/1991 | Tu et al. | |
| 5,476,589 A | 12/1995 | Bacino | |
| 5,534,007 A | 7/1996 | St. Germain et al. | |
| 5,549,663 A | 8/1996 | Cottone | |
| 5,708,044 A | 1/1998 | Branca | |
| 5,718,973 A | 2/1998 | Lewis et al. | |
| 5,752,934 A | 5/1998 | Campbell et al. | |
| 5,759,192 A | 6/1998 | Saunders | |
| 5,769,884 A | 6/1998 | Solovay | |
| 5,772,884 A | 6/1998 | Tanaka et al. | |
| 5,824,043 A | 10/1998 | Cottone | |
| 5,843,158 A | 12/1998 | Lenker et al. | |
| 5,843,161 A | 12/1998 | Solovay | |
| 5,853,419 A | 12/1998 | Imran | |
| 5,925,061 A | 7/1999 | Ogi et al. | |
| 5,935,162 A | 8/1999 | Dang | |
| 6,010,529 A | 1/2000 | Herweck et al. | |
| 6,013,854 A | 1/2000 | Moriuchi | |
| 6,042,588 A | 3/2000 | Munsinger et al. | |
| 6,042,605 A | 3/2000 | Martin et al. | |
| 6,042,606 A | 3/2000 | Frantzen | |
| 6,174,329 B1 | 1/2001 | Callol et al. | |
| 6,190,406 B1 | 2/2001 | Duerig et al. | |
| 6,217,609 B1 | 4/2001 | Haverkost | |
| 6,245,012 B1 | 6/2001 | Kleshinski | |
| 6,261,320 B1 | 7/2001 | Tam et al. | |
| 6,261,620 B1 | 7/2001 | Leadbeater | |
| 6,336,937 B1 * | 1/2002 | Vonesh | A61F 2/07 623/1.13 |
| 6,352,552 B1 | 3/2002 | Levinson et al. | |
| 6,436,132 B1 | 8/2002 | Patel et al. | |
| 6,488,701 B1 | 12/2002 | Nolting et al. | |
| 6,541,589 B1 | 4/2003 | Baillie | |
| 6,620,190 B1 | 9/2003 | Colone | |
| 6,626,939 B1 | 9/2003 | Burnside et al. | |
| 6,673,107 B1 | 1/2004 | Brandt et al. | |
| 6,730,120 B2 | 5/2004 | Berg et al. | |
| 6,755,856 B2 | 6/2004 | Fierens et al. | |
| 6,758,858 B2 | 7/2004 | McCrea et al. | |
| 7,049,380 B1 | 5/2006 | Chang et al. | |
| 7,083,642 B2 | 8/2006 | Sirhan et al. | |
| 7,105,018 B1 | 9/2006 | Yip et al. | |
| 7,306,729 B2 | 12/2007 | Bacino et al. | |
| 7,419,678 B2 | 9/2008 | Falotico | |
| 7,531,611 B2 | 5/2009 | Sabol et al. | |
| 7,789,908 B2 | 9/2010 | Sowinski et al. | |
| 7,811,314 B2 | 10/2010 | Fierens et al. | |
| 7,815,763 B2 | 10/2010 | Fierens et al. | |
| 7,927,364 B2 | 4/2011 | Fierens et al. | |
| 7,927,365 B2 | 4/2011 | Fierens et al. | |
| 7,935,141 B2 | 5/2011 | Randall et al. | |
| 7,967,829 B2 | 6/2011 | Gunderson et al. | |
| 8,585,753 B2 | 11/2013 | Scanlon | |
| 9,345,601 B2 | 5/2016 | Jantzen | |
| 2002/0198588 A1 | 12/2002 | Armstrong et al. | |
| 2003/0055494 A1 * | 3/2003 | Bezuidenhout | A61F 2/04 623/1.39 |
| 2003/0060871 A1 | 3/2003 | Hill et al. | |
| 2003/0180488 A1 | 9/2003 | Lim et al. | |
| 2004/0024442 A1 * | 2/2004 | Sowinski | A61L 27/16 623/1.13 |
| 2004/0024448 A1 | 2/2004 | Chang et al. | |
| 2004/0133266 A1 | 7/2004 | Clerc et al. | |
| 2004/0170782 A1 | 9/2004 | Wang et al. | |
| 2004/0260277 A1 | 12/2004 | Maguire | |
| 2005/0080476 A1 | 4/2005 | Gunderson et al. | |
| 2005/0137680 A1 | 6/2005 | Ortiz et al. | |
| 2005/0283224 A1 | 12/2005 | King | |
| 2006/0009835 A1 | 1/2006 | Osborne et al. | |
| 2006/0036311 A1 | 2/2006 | Nakayama et al. | |
| 2006/0106337 A1 | 5/2006 | Blankenship | |
| 2006/0135985 A1 | 6/2006 | Cox et al. | |
| 2006/0161241 A1 | 7/2006 | Barbut et al. | |
| 2006/0259133 A1 | 11/2006 | Sowinski et al. | |
| 2006/0271091 A1 | 11/2006 | Campbell et al. | |
| 2006/0276883 A1 | 12/2006 | Greenberg et al. | |
| 2007/0012624 A1 | 1/2007 | Bacino et al. | |
| 2007/0060999 A1 | 3/2007 | Randall et al. | |
| 2007/0129786 A1 | 6/2007 | Beach et al. | |
| 2007/0207186 A1 | 9/2007 | Scanlon et al. | |
| 2007/0207816 A1 | 9/2007 | Spain | |
| 2007/0208421 A1 | 9/2007 | Quigley | |
| 2007/0213800 A1 | 9/2007 | Fierens et al. | |
| 2007/0250146 A1 | 10/2007 | Cully et al. | |
| 2007/0250153 A1 * | 10/2007 | Cully | A61F 2/07 623/1.13 |
| 2007/0254012 A1 | 11/2007 | Ludwig et al. | |
| 2008/0051876 A1 | 2/2008 | Ta et al. | |
| 2008/0097582 A1 | 4/2008 | Shanley et al. | |
| 2008/0119943 A1 | 5/2008 | Armstrong et al. | |
| 2008/0319531 A1 | 12/2008 | Doran et al. | |
| 2009/0005854 A1 | 1/2009 | Huang et al. | |
| 2009/0030499 A1 | 1/2009 | Bebb et al. | |
| 2009/0043373 A1 | 2/2009 | Arnault de la Menardiere et al. | |
| 2009/0182413 A1 | 7/2009 | Burkart et al. | |
| 2010/0094394 A1 | 4/2010 | Beach et al. | |
| 2010/0094405 A1 | 4/2010 | Cottone | |
| 2010/0106240 A1 | 4/2010 | Duggal et al. | |
| 2010/0159171 A1 | 6/2010 | Cough | |
| 2010/0256738 A1 | 10/2010 | Berglund | |
| 2012/0323211 A1 | 12/2012 | Ogle et al. | |
| 2013/0131780 A1 | 5/2013 | Armstrong et al. | |
| 2013/0184807 A1 | 7/2013 | Kovach et al. | |
| 2013/0253466 A1 | 9/2013 | Campbell et al. | |
| 2013/0297003 A1 | 11/2013 | Pinchuk | |
| 2014/0135897 A1 | 5/2014 | Cully et al. | |
| 2014/0172066 A1 | 6/2014 | Goepfrich et al. | |
| 2014/0180402 A1 | 6/2014 | Bruchman et al. | |
| 2015/0313871 A1 | 11/2015 | Li et al. | |
| 2016/0015422 A1 | 1/2016 | De Cicco et al. | |

FOREIGN PATENT DOCUMENTS

| | | |
|---|---|---|
| EP | 0 815 806 | 1/1997 |
| EP | 0 893 108 | 1/1999 |
| JP | H09241412 A | 9/1997 |
| JP | H11290448 A | 10/1999 |
| JP | 2001509702 A | 7/2001 |
| JP | 2010504174 A | 2/2010 |
| JP | 2010535075 A | 11/2010 |
| WO | WO9416802 A1 | 8/1994 |
| WO | 95/05555 | 2/1995 |
| WO | 97/10871 | 3/1997 |
| WO | 00/41649 | 7/2000 |
| WO | WO0047271 A1 | 8/2000 |
| WO | 01/74272 | 10/2001 |
| WO | 02/060506 | 8/2002 |
| WO | 2004/000375 | 12/2003 |
| WO | 2006019626 A2 | 2/2006 |
| WO | 2008/021002 | 2/2008 |
| WO | 2008/028964 | 3/2008 |
| WO | 2008/036870 | 3/2008 |
| WO | 2008/049045 | 4/2008 |
| WO | 2009017827 A1 | 2/2009 |
| WO | 2009/100210 | 8/2009 |
| WO | 2009108355 A1 | 9/2009 |
| WO | 2010006783 A1 | 1/2010 |
| WO | 2010008570 A1 | 1/2010 |
| WO | 2010/030766 | 3/2010 |
| WO | 2010/132707 | 11/2010 |
| WO | WO 2011/098565 * | 8/2011 |
| WO | 2013/109337 | 7/2013 |

OTHER PUBLICATIONS

International Search Report for PCT/US2012/065066, dated Nov. 11, 2013, corresponding to U.S. Appl. No. 13/675,959, 10 pages.
Google Image Search Results, "S-Shaped", accessed Nov. 1, 2013.

(56) References Cited

OTHER PUBLICATIONS

International Search Report for PCT/US2013/076405 dated May 6, 2014,corresponding to U.S. Appl. No. 14/132,767, 8 pages.
International Search Report for PCT/US2014/013496 dated Dec. 2, 2014,corresponding to U.S. Appl. No. 13/755,481, 4 pages.
International Search Report and Written Opinion for PCT/US2011/061165 dated Oct. 1, 2012, corresponding to U.S. Appl. No. 13/298,060.
Nakayama, Yasuhide. Microporous Stent Achieves Brain Aneurysm Occlusion Without Disturbing Branching Flow. NeuroNews Nov. 2012; 8:1-2.
Nishi S, Nakayama Y, Ishibashi-Ueda H, Okamoto Y, Yoshida M. Development of microporous self-expanding stent grafts for treating cerebral aneurysms: designing micropores to control intimal hyperplasia. J Artif Organs 2011; 14:348-356.
International Search Report and Written Opinion for PCT/US2012/064908 dated Feb. 4, 2013, corresponding to U.S. Appl. No. 13/675,730, 11 pages.
International Search Report and Written Opinion for PCT/US2012/066518, dated Feb. 4, 2013, corresponding to U.S. Appl. No. 13/351,052, 12 pages.
International Search Report and Written Opinion issued in PCT/US2016/028671, dated Jul. 28, 2016, 19 pages.

* cited by examiner

ELASTIC STENT GRAFT

CROSS-REFERENCE TO RELATED APPLICATION

This application is a continuation in part of and claims priority to U.S. Non-Provisional Ser. No. 13/675,764, filed on Nov. 13, 2012 and entitled "Elastic Stent Graft", wherein such non-provisional application is hereby incorporated by reference in its entirety.

FIELD OF THE INVENTION

The present invention relates generally to medical implants for supporting, maintaining, or repairing a lumen, passageway, or opening in a living body, and more particularly, to a stent having thereon a covering that includes (1) an expanded polytetrafluoroethylene (ePTFE) membrane containing serpentine fibrils and (2) an elastomer.

Definitions

As used herein, the term "serpentine fibrils" means multiple fibrils that curve or turn one way then another.

As used herein, the term "controlled retraction" refers to causing articles to shorten in length in at least one direction by the application of heat, by wetting with a solvent, or by any other suitable means or combinations thereof in such a way as to inhibit folding, pleating, or wrinkling of the subsequent article visible to the naked eye.

The term "imbibed or imbibing" as used herein is meant to describe any means for at least partially filling at least a portion of the pores of a porous material such as ePTFE or the like.

The term "elastic" as used herein refers to the property of a material to be elongated upon the application of a force and that returns to its approximate original dimensions upon the release of the force due to the retraction force of the material.

The term "elongation" or "elongated" as used herein is meant to denote the increase in length in response to the application of a force.

The term "elastic" as used herein refers to the property of a material to be elongated upon the application of a force and that returns to its approximate original dimensions upon the release of the force due to the retraction force of the material.

The term "increase in stiffness" as used herein refers the increase in resistance to further elongation once the stop-point is reached.

For purposes of this invention, the entire device is considered to be "wrinkle-free" if within a 1 cm length of the device, the graft portion is devoid of wrinkles and folds. It is to be noted that the terms "free of folds", "devoid of folds", and "fold free" are used interchangeably herein.

BACKGROUND OF THE INVENTION

Conventional vascular grafts have long been used for vascular repair in humans and animals. These devices are typically flexible tubes of woven or knitted polyethylene terephthalate or porous polytetrafluoroethylene (hereinafter PTFE). Grafts of biological origin have also been used, these being typically fixed human umbilical or bovine arteries. Such conventional vascular grafts usually require invasive surgical methods that expose at least both ends of the segment of the vessel to be repaired. Frequently it is necessary to expose the entire length of the vessel segment. These types of repairs cause major trauma to the patient with corresponding lengthy recovery periods and occasionally, even death.

Alternative methods have evolved which use intraluminal vascular grafts in the form of adjustable stent structural supports, tubular grafts, or a combination thereof. These devices are preferably remotely introduced into a body cavity by the use of a catheter type of delivery system. Alternatively, they may be directly implanted by invasive surgery. The intent of these methods is to maintain patency after an occluded vessel has been re-opened using balloon angioplasty, laser angioplasty, atherectomy, roto-ablation, invasive surgery, or a combination of these treatments.

Intraluminal vascular grafts can also be used to repair aneurysmal vessels, particularly aortic arteries, by inserting an intraluminal vascular graft within the aneurysmal vessel so that the prosthetic device withstands the blood pressure forces responsible for creating the aneurysm. In addition, intraluminal vascular grafts provide a new blood contacting surface within the lumen of a diseased living vessel.

If the intraluminal graft used has a thin enough wall and adequate flexibility, it may be collapsed and inserted into a body conduit at a smaller diameter and at a location remote from the intended repair site. A catheter type of delivery system is then used to move the intraluminal graft into the repair site and then expand its diameter appropriately to conform to the inner surface of the living vessel. Various attachment methods including the use of adjustable stents may be used to secure the intraluminal graft at the desired location without the necessity of invasive surgery.

Stent grafts (or covered stents) have been used extensively where external support, such as in the form of rings, spirals, or metal frames with a multiplicity of openings, and the like are required when the application or patient anatomy may exert forces that either could crush or collapse the intraluminal device were it not for the presence of the support. A support is also required in situations where the internal pressure on the device would result in undesirable diametric growth of the device were it not for the presence of the support. Stent grafts can take many forms and may be constructed of a wide variety of materials including, but not limited to, stainless steel, tantalum, nitinol stent materials and polyurethane, ePTFE, and Dacron cover materials.

SUMMARY OF THE INVENTION

It is an object of the present invention to utilize fluoropolymer membranes that exhibit high elongation while substantially retaining the strength properties of the fluoropolymer membrane. Such fluoropolymer membranes characteristically possess serpentine fibrils.

It is another object of the present invention to provide a stent graft that includes (1) a stent having a wall with at least one opening, an outer surface, and an inner surface, and (2) a cover affixed to the stent. The cover may be affixed to the outer surface and/or the inner surface. Additionally, the cover includes a composite material that includes at least one expanded fluoropolymer membrane and an elastomer. The composite material has a stop point at which no further expansion, elongation, or both occur. That is, the composite material can be radially expanded or elongated to a point at which further expansion is inhibited by a dramatic increase in stiffness. The expanded fluoropolymer membrane includes serpentine fibrils. In one exemplary embodiment, the fluoropolymer is polytetrafluoroethylene. The fluoropolymer membrane may include a microstructure of substantially only serpentine fibrils. In at least one embodiment, the fluoropolymer membrane may include a plurality of serpentine fibrils. The serpentine fibrils have a width of about 1.0 micron or less. The endoprosthetic device expands and contracts radially after deployment into a vessel in a body without the cover infolding into the vessel. The cover can remain wrinkle-free when radially expanded at about 80% of the nominal diameter and greater. Further, the composite material can be free of wrinkles before loading and after deployment of the endoprosthetic device to a nominal diameter.

It is yet another object of the present invention to provide an intraluminal stent graft that includes (1) a stent having a wall with at least one opening, an outer surface, and an inner surface and (2) a cover that includes a composite material that contains at least one expanded fluoropolymer membrane having serpentine fibrils and an elastomer. The serpentine fibrils have a width of about 1.0 micron or less. The cover is provided on at least one surface of the stent and covers at least a portion of the opening. The elastomer may be positioned on the fluoropolymer membrane and/or in all or substantially all of the pores of the fluoropolymer membrane. In exemplary embodiments, the fluoropolymer is polytetrafluoroethylene. The cover can be optionally used to cover the outside and/or the inside of the stent. In addition, the cover possesses good flexibility. Additionally, the composite material has a stop point at which no further expansion occurs. That is, the composite material may be radially expanded to a point at which further expansion is inhibited by a dramatic increase in stiffness. Also, the cover can be designed to distend at a relatively low pressure until a predetermined diameter is achieved. Upon reaching that predetermined diameter, significantly higher pressures are required to further distend the stent graft. The stent graft has a migration resistance that is similar to devices that contain barbs that penetrate the vessel.

It is also an object of the present invention to provide an intraluminal graft that includes a tubular support member that contains a composite material that includes at least one expanded fluoropolymer membrane and an elastomer where the tubular support has elastic properties in the axial direction of the support. The expanded fluoropolymer membrane includes serpentine fibrils. The serpentine fibrils have a width of about 1.0 micron or less. In exemplary embodiments, the fluoropolymer is polytetrafluoroethylene. The elastomer may be present in all or substantially all of the pores of the expanded fluoropolymer membrane. Additionally, the fluoropolymer membrane may include a microstructure of substantially only serpentine fibrils. In one or more exemplary embodiments, the fluoropolymer membrane includes a plurality of serpentine fibrils. The composite material has a stop point at which no further expansion occurs. That is, the composite material can be radially expanded to a point at which further expansion is inhibited by a dramatic increase in stiffness.

It is a further object of the present invention to provide a method of manufacturing a stent graft that includes (1) positioning a cover including a composite material on at least one surface of a stent at a nominal diameter of the stent to form a stent graft and (2) permitting the cover to bond to the stent at substantially room temperature. The composite material includes at least one expanded fluoropolymer membrane and an elastomer. The cover may be positioned on the outer surface and/or the inner surface of the stent. An adhesive may be applied to the stent prior to positioning the cover on the stent. In at least one exemplary embodiment, the expanded fluoropolymer membrane includes a microstructure of substantially only serpentine fibrils. The fluoropolymer membrane may include a plurality of serpentine fibrils. The serpentine fibrils have a width of about 1.0 micron or less.

It is also an object of the present invention to provide an intraluminal stent graft that includes (1) a stent having a wall with at least one opening, an outer surface, and an inner surface and (2) a cover including a composite material that exhibits an increase in stiffness when expanded to at least about 14 mm. The cover is provided on at least one of the outer surface and the inner surface and covers at least a portion of the at least one opening. The composite material includes at least one expanded fluoropolymer membrane and an elastomer. Additionally, the expanded fluoropolymer may include a microstructure of serpentine fibrils. In one exemplary embodiment, the fluoropolymer membrane may include a plurality of serpentine fibrils. The serpentine fibrils have a width of about 1.0 micron or less.

It is yet another object of the present invention to provide an intraluminal graft that includes a tubular support member including (1) a composite material exhibiting an increase in stiffness when expanded to at least about 14 mm and (2) an elastomer. The tubular support member has elastic properties in the axial direction of the tubular support member.

It is an advantage of the present invention that an endoprosthetic device containing the composite material is free or substantially free of folds when radially expanded to about 80% of its nominal diameter.

It is also an advantage of the present invention that a stent graft can be manufactured at the stent nominal diameter.

It is a feature of the present invention that endoprosthetic devices utilizing the inventive elastomeric composite material demonstrate improved migration resistance.

It is another advantage of the present invention that the stent graft can be implanted undersized with respect to a nominal diameter without having material infolding.

It is another feature of the present invention that an elastic stent graft is formed that has regions of compression and extension without material folding.

It is yet another feature of the present invention that the stent graft may have elastic properties longitudinally, radially, or both longitudinally and radially.

The foregoing and other objects, features, and advantages of the invention will appear more fully hereinafter from a consideration of the detailed description that follows. It is to be expressly understood, however, that the drawings are for illustrative purposes and are not to be construed as defining the limits of the invention.

BRIEF DESCRIPTION OF THE FIGURES

The advantages of this invention will be apparent upon consideration of the following detailed disclosure of the invention, especially when taken in conjunction with the accompanying drawings wherein.

DETAILED DESCRIPTION OF THE INVENTION

Figure 1:
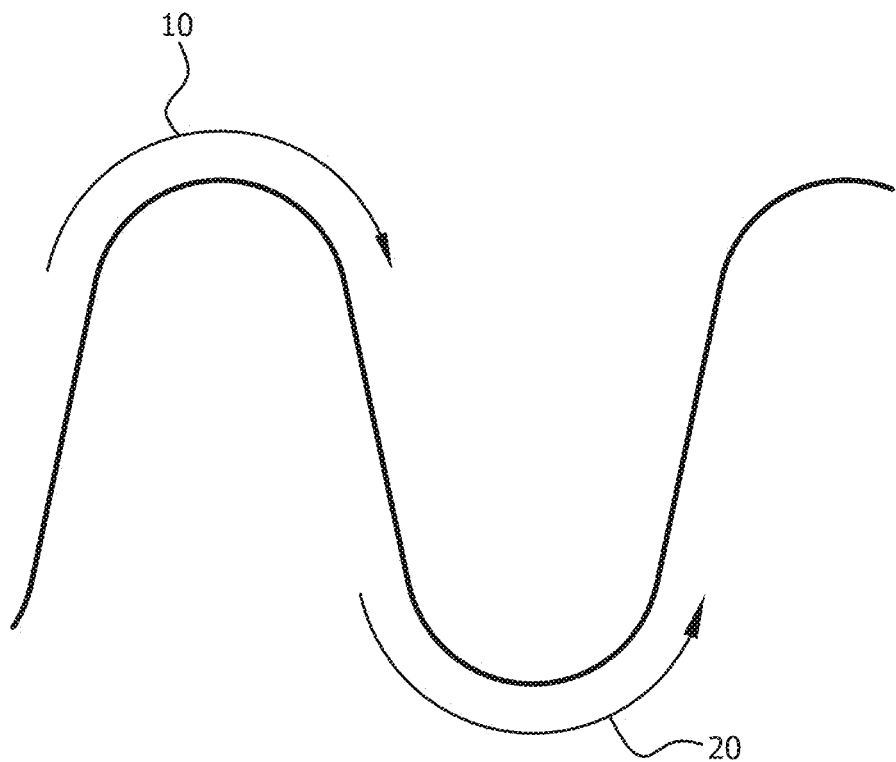
FIG. 1 is a schematic illustration of an exemplary, idealized serpentine fibril.

Unless defined otherwise, all technical and scientific terms used herein have the same meaning as commonly understood by one of ordinary skill in the art to which the invention belongs. In the drawings, the thickness of the lines, layers, and regions may be exaggerated for clarity. Like numbers found throughout the figures denote like elements. The terms "graft" and "cover" may be used interchangeably herein. In addition, the terms "stent graft" and "covered stent" may be used interchangeably herein to describe a stent having a cover thereon.

The present invention is directed to a stent having thereon a graft that includes a composite material including (1) an expanded polytetrafluoroethylene (ePTFE) membrane containing serpentine fibrils and (2) an elastomer. The elastomer may be positioned on the ePTFE membrane and may also, or alternatively, be located in at least a portion of the pores of the ePTFE membrane. The elastomer may be present in all or substantially all of the pores of the ePTFE membrane. The term "substantially all of the pores" as used herein is meant to denote that the elastomer is present in at least a portion of all or nearly all of the pores of the ePTFE membrane. In one or more exemplary embodiment, the stent includes a fluoropolymer membrane.

The stent graft and tubes of the invention may be employed in any body conduit or vessel, including arteries and veins. Stent covers enable the exclusion of aneurysms and inhibit the passage of body fluids across the walls of the stent. The stent cover can be optionally used to cover the outside and/or the inside of the stent or other support structures. It is to be understood that a tube formed of the inventive composite material can be used without covering a stent.

One benefit of the instant invention is that the elastic properties in the radial direction of a stand alone tube (which could serve as an intraluminal graft) or the graft portion of the stent graft remains fold-free when radially contracted about 80%, or conversely, the graft portion of the stent graft is fold-free when radially expanded to about 80% and greater. Indeed, depending on the manner of construction, a stent graft or tube formed with the inventive composite material (cover) can expand and/or contract radially after being deployed without having or reducing the amount of material infolding, thereby minimizing obstructions that can cause thrombosis. The absence of folds while implanted has significant clinical ramifications, as folds in the graft portion may serve as sites of thrombus accumulation that can ultimately result in total occlusion of the device. One significant importance of the device being fold-free is the reduction or elimination of thrombic depositions. For purposes of this invention, the entire device is considered to be "wrinkle-free" if within a 1 cm length of the device, the graft portion is devoid of wrinkles and folds when viewed by the naked eye. It is to be noted that 1 cm length of the device should be used unless the entire length of the device is less than 1 cm. In that instance, the entire device should be utilized to determine if the device is "wrinkle-free." Consequently, should the stent graft be implanted undersized, no folds are present in the cover. Furthermore, if needed, the covered stent can be elastically expanded beyond the nominal stent diameter (La, the labeled diameter) when the cover is constructed to have a stop point greater than the nominal diameter.

In another embodiment of the invention, a tube or stent graft can be constructed such that the elastic properties are present in the longitudinal direction of the device. A longitudinally stretchable stent graft prevents infolding of the graft into the lumen as discussed above. One advantage of a longitudinally stretchable stent graft is that when the stent graft is presented with a tortuous path, the inventive stent graft is able to bend without kinking when placed in a body conduit arch. More specifically, the tension side of the bend can stretch and the compression side of the bend can compress without wrinkling the composite material (cover). The stretching of the composite material permits for a smooth flow through the stent graft as little or no wrinkling occurs.

The composite material may also be used to construct circumferentially-, helically-, or axially-oriented tubes and covers, as well as combinations thereof. As used herein, the term "axial" is interchangeable with the term longitudinal." When the composite material is applied helically, elasticity is imparted in both the longitudinal and circumferential directions. It was surprisingly discovered that there is an absence of folds in an axially formed cover material when the stent graft is both compacted and expanded to about 80% of the nominal diameter. The cover can be formed prior to application to a stent (i.e., a separate cover can be made in the shape of a tube from the composite material). Alternatively, the cover can be formed after the composite material has been applied to the stent, after which the composite material is bonded both to itself and to the stent.

Stent grafts with minimal or no material infolding are able to accommodate the natural tapering of vessels to a greater degree than conventionally known devices. Additionally, tubes and stent grafts formed from the inventive composite material have improved migration resistance compared to conventional devices.

The cover of the present invention is unique in that it is fold-free or substantially fold-free as implanted; e.g., the cover can be substantially fold-free when radially expanded to about 80% and up to about 100% of the nominal diameter or greater. In addition, the cover is unique in that it exhibits a sharp increase in stiffness at a predetermined diameter. This latter property creates a "stop-point" beyond which increased balloon pressure does not further increase the covered stent diameter. One advantage of the feature of the stop point is that the stent graft does not itself become aneurismal. The tubes and stent grafts of the present invention can be designed to have a stop point in either a radial or axial direction.

An additional benefit of the present invention is that the tube or the cover portion of a stent graft can be designed to distend at a relatively low pressure until a predetermined diameter is achieved. Upon reaching that diameter, significantly higher pressures are required to further distend the tube or stent graft. In other words, the slope of the diameter versus pressure curve decreases dramatically once the predetermined diameter is reached.

Figure 6:
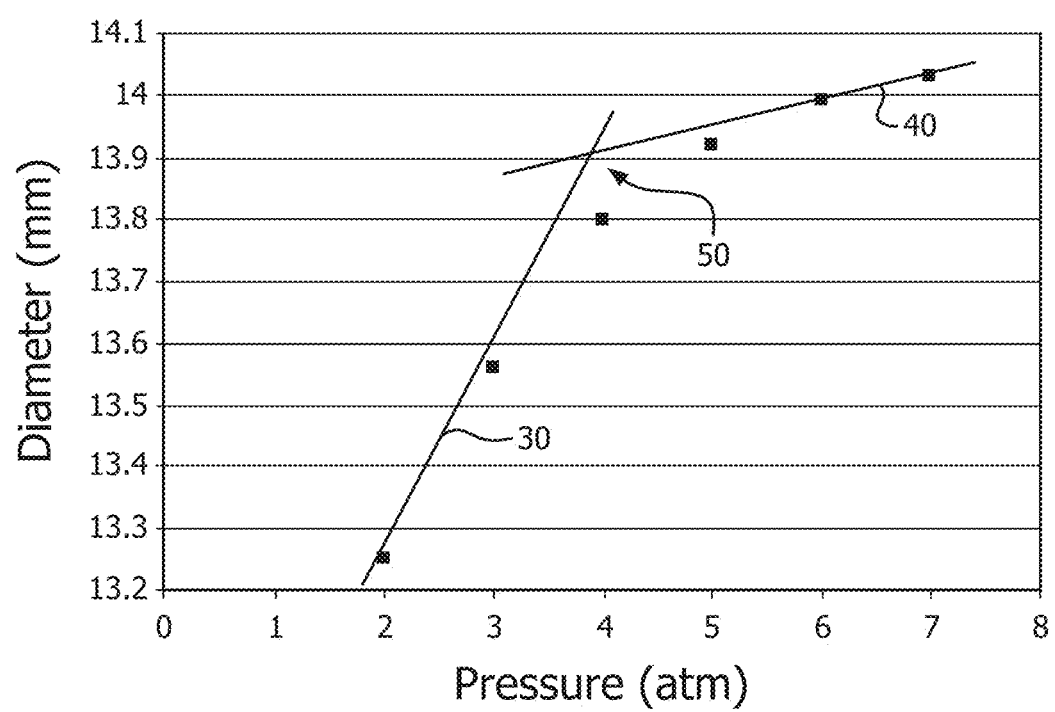
FIG. 6 is a pressure vs. diameter curve corresponding to a helically wrapped tube according to the present invention.

Pressure-diameter curves relating to tubes and covered stents of the present invention exhibit an inflection point due to the change in slope (which is directly related to the stiffness) upon reaching a diameter referred to herein as the stop point. FIG. 6 is a pressure vs. diameter curve of an article according to the present invention, in this case a tube, in which the intersection of two tangent lines depicts the stop point of the article. An estimate of the stop point may be determined in the following manner. The slope of the pressure-diameter curve prior to reaching the stop point can be approximated by drawing a straight line tangent to the curve, shown as line 30 in FIG. 6. The slope of the pressure-diameter curve beyond the stop point can be approximated by drawing a straight line tangent to the curve, shown as line 40 in FIG. 6. The diameter corresponding to the intersection of the two tangent lines, depicted by reference numeral 50, is an estimation of the stop point for the article.

A stent graft according to the invention can advantageously be constructed at the stent nominal (i.e., labeled) diameter, or a larger diameter. In particular, a cover formed of the composite material can be positioned on the outer and/or inner surface of the stent with the stent at the nominal stent diameter. In one embodiment, the composite material is at least partially elongated upon application to the stent (e.g., by wrapping the material around the stent) at its nominal diameter, or larger than nominal diameter. In an alternate embodiment, the composite material may be stretched until the composite material is at least partially elongated prior to or during the positioning of a tubular cover on the stent. For example, a cover having a substantially smaller diameter than the nominal diameter of the stent can be employed to cover the stent at least partially due to the elasticity of the composite material. The range within which the cover can be wrinkle-free can be at least about 80% of the nominal diameter and greater During construction of a tube or a cover for a stent graft, the amount of tension applied to the composite material when forming can be adjusted to adjust the elastic range (or wrinkle-free range) of the cover and the stop point. For example, if the composite material is applied to a stent at nominal diameter with near complete elongation, the stop point will be approximately the nominal diameter, and the amount of compaction permitted while remaining wrinkle free and the amount of expansion permitted while remaining wrinkle free is at a maximum for that composite material. However, if the same composite material is applied to the same stent with only partial elongation, the stop point will be at a diameter greater than the nominal diameter, and the amount of compaction and expansion permitted while remaining wrinkle free is less than the former.

The cover can be bonded to the stent at or substantially at room temperature. Unlike some conventional processes, no cold crushing or other similar process steps is involved. An adhesive, such as an adhesive copolymer, may be applied to the stent prior to positioning the cover on the outer surface and/or the inner surface of the stent to bond the cover to the stent.

Another advantage of the present invention is the ability of the stent graft to be expanded in situ to dislodge a clot or other adhesion on the inner surface. In particular, the at least partially occluded covered stent may be expanded to a larger diameter through the use of a balloon catheter, thereby dislodging the stenotic material. A protective measure could be used to capture the stenotic material to prevent stroke, thrombosis, or other unwanted, deleterious side effects. Upon release of the pressure of the balloon, the covered stent returns at least substantially to its previous diameter without wrinkling.

In at least one embodiment of the present invention, fluoropolymer membranes that exhibit high elongation while substantially retaining the strength properties of the fluoropolymer membrane are utilized as the cover material. Such membranes characteristically possess serpentine fibrils, such as the idealized serpentine fibril exemplified in FIG. 1. As depicted generally in FIG. 1, a serpentine fibril curves or turns generally one way in the direction of arrow 10 then generally another way in the direction of arrow 20. It is to be understood that the amplitude, frequency, and periodicity of the serpentine-like fibrils as exemplified in FIG. 1 may vary. In one embodiment, the fluoropolymer membranes are expanded fluoropolymer membranes. Non-limiting examples of expandable fluoropolymers include, but are not limited to, expanded PTFE, expanded modified PTFE, and expanded copolymers of PTFE. Patents have been filed on expandable blends of PTFE, expandable modified PTFE, and expanded copolymers of PTFE, such as, for example, U.S. Pat. No. 5,708,044 to Branca; U.S. Pat. No. 6,541,589 to Baillie; U.S. Pat. No. 7,531,611 to Sabol et al.; U.S. patent application Ser. No. 11/906,877 to Ford; and U.S. patent application Ser. No. 12/410,050 to Xu et al.

The high elongation is enabled by forming relatively straight fibrils into serpentine fibrils that substantially straighten upon the application of a force in a direction opposite to the compressed direction. The creation of the serpentine fibrils can be achieved through a thermally-induced controlled retraction of the expanded polytetrafluoroethylene (ePTFE), through wetting the article with a solvent, such as, but not limited to, isopropyl alcohol or Fluorinert® (a perfluorinated solvent commercially available from 3M, Inc., St. Paul, Minn.), or by a combination of these two techniques. The retraction of the article does not result in visible pleating, folding, or wrinkling of the ePTFE, unlike what occurs during mechanical compression. The retraction also can be applied to very thin membranes, unlike known methods. During the retraction process, the fibrils not only become serpentine in shape but also may also increase in width.

The precursor materials can be biaxially expanded ePTFE membranes. In one embodiment, materials such as those made in accordance with the general teachings of U.S. Pat. No. 7,306,729 to Bacino, et al. are suitable precursor membranes, especially if small pore size articles are desired. These membranes may possess a microstructure of substantially only fibrils. The precursor membrane may or may not be amorphously locked. Additionally, the precursor membrane may be at least partially filled, coated, or otherwise combined with additional materials.

The precursor membrane may be restrained in one or more directions during the retraction process in order to prescribe the desired amount of elongation of the final article. The amount of elongation is directly related to, and is determined by, the amount of retraction.

In one embodiment, retraction can be achieved in a uniaxial tenter frame by positioning the rails at a distance less than the width of the precursor membrane prior to the application of heat or solvent or both. When using a biaxial tenter frame, one or both of the sets of grips, pins, or other suitable attachment means can similarly be positioned at a distance less than the dimensions of the precursor membrane. It is to be appreciated that these retraction means differ from the mechanical compression taught by the House and Sowinski patents noted above. Upon retraction, the expanded fluoropolymer membrane possesses serpentine fibrils. These retracted membranes characteristically possess serpentine fibrils and are substantially wrinkle free. In some exemplary embodiments, the retracted membranes may possess a microstructure of substantially only serpentine fibrils. In at least one embodiment, the fluoropolymer membranes include a plurality of serpentine fibrils. As used herein, the phrase "plurality of serpentine fibrils" is meant to denote the presence of 2 or more, 5 or more, 10 or more, or 15 or more serpentine fibrils in the fluoropolymer membrane within a field of view as taught below. The serpentine fibrils have a width of about 1.0 micron or less, and in some embodiments, about 0.5 microns or less. In one embodiment, the serpentine fibrils have a width from about 0.1 to about 1.0 microns, or from about 0.1 to about 0.5 microns.

The precursor membranes described above can be imbibed with an elastomeric material prior, during, or subsequent to retraction to form a composite material. In the absence of such elastomeric materials, fluoropolymer articles having serpentine fibrils do not exhibit appreciable recovery after elongation. Suitable elastomeric materials include, but are not limited to, PMVE-TFE (perfluoromethylvinyl ether-tetrafluoroethylene) copolymers, PAVE-TFE (perfluoro(alkyl vinyl ether)-tetrafluoroethylene) copolymers, silicones, polyurethanes, and the like. It is to be noted that PMVE-TFE and PAVE-TFE are fluoroelastomers.

Having generally described this invention, a further understanding can be obtained by reference to certain specific examples illustrated below which are provided for purposes of illustration only and are not intended to be all inclusive or limiting unless otherwise specified.

Testing Methods

It should be understood that although certain methods and equipment are described below, any method or equipment determined suitable by one of ordinary skill in the art may be alternatively utilized.

Mass, Thickness, and Density

Membrane samples were die cut to form rectangular sections about 2.54 cm by about 15.24 cm to measure the weight (using a Mettler-Toledo analytical balance model AG204) and thickness (using a Käfer Fz1000/30 snap gauge). Using these data, density was calculated with the following formula: $\rho=m/(w*l*t)$, in which: $\rho$=density (g/cm$^3$), m=mass (g), w=width (cm), l=length (cm), and t=thickness (cm). The average of three measurements was reported.

Matrix Tensile Strength (MTS) of Membranes

Tensile break load was measured using an INSTRON 122 tensile test machine equipped with flat-faced grips and a 0.445 MI load cell. The gauge length was about 5.08 cm and the cross-head speed was about 50.8 cm/min. The sample dimensions were about 2.54 cm by about 15.24 cm. For highest strength measurements, the longer dimension of the sample was oriented in the highest strength direction. For the orthogonal MTS measurements, the larger dimension of the sample was oriented perpendicular to the highest strength direction. Each sample was weighed using a Mettler Toledo Scale Model AG204, then the thickness was measured using the Käfer FZ1000/30 snap gauge; alternatively, any suitable means for measuring thickness may be used. The samples were then tested individually on the tensile tester. Three different sections of each sample were measured. The average of the three maximum loads peak force) measurements was reported. The longitudinal and transverse matrix tensile strengths (MTS) were calculated using the following equation: MTS=(maximum load/cross-section area)*(bulk density of PTFE)/(density of the porous membrane), where the bulk density of the PTFE was taken to be about 2.2 g/cm$^3$.

Scanning Electron Microscopy

Scanning electron micrographs were created choosing magnifications suitable for identifying fibrils. Articles that have been retracted in accordance with the teachings of invention may require elongation in the direction of retraction in order to identify the serpentine fibrils. For the purposes of identifying the number of serpentine fibrils, a field of view of 7 microns by 7 microns of the sample is to be employed.

In addition, for the purpose of characterizing fibril width, measurements should be made for serpentine fibrils that are substantially separated from each other and do not band together or otherwise form series of fibrils paralleling each other within the membrane. To determine the fibril width, a line is drawn through the SEM image to bisect it. The SEM image should be of sufficient magnification such that at least 5 serpentine fibrils and not more than 20 serpentine fibrils are clearly visible within the SEM image. Starting from one edge of the bisected image, the width of the first five consecutive serpentine fibrils that intersect the bisecting line is measured. The measurements are made where the fibril intersects the bisecting line. Next, the five measurements are averaged and the average measurement is recorded.

Removal of Elastomer from a Stent Cover

For a tube or a stent cover containing an elastomer, the elastomer can be dissolved or degraded and subsequently rinsed away using an appropriate solvent in order to measure or examine desired properties.

For instance, the fluoroelastomer component of a tube or a stent cover as described in Examples 2-5 can be partially or substantially removed to enable SEM imaging of the ePTFE structure. The sample is submerged in 95 g of Fluorinert® Electronic Liquid FC-72 (3M Inc., St. Paul, Minn.) and allowed to soak without agitation. After approximately one hour, the fluorinated solvent is poured off and replaced with 95 g of fresh solvent. This process is repeated for a total of 5 soaking cycles, the first 4 cycles for approximately 1 hour, and the 5th cycle for approximately 24 hours.

To aid in the removal of elastomer, the sample can also be agitated using an ultrasonic cleaner (e.g. Branson 200 Ultrasonic Cleaner (Model—B200)).

Pressure vs. Diameter Test

A pressure versus diameter curve is created by radially expanding a tube or covered stent using an inflation syringe to pressurize a balloon catheter. The tube or covered stent is positioned over the balloon catheter in its deflated state. The tube or covered stent diameter is measured at 1 ATM intervals using a laser micrometer.

For example, a 14 mm balloon diameter with a 20 mm balloon length and a 0.035 inch guide wire Peripheral Dilation Catheter (Agilitrac, Abbott Vascular, Santa Clara, Calif.) and a Basix™ COMPAK (Merit Medical, South Jordan, Utah) inflation syringe were used. The handle on the inflator was slowly turned while the change in pressure as indicated on the dial was observed. The balloon was then inflated to 2 atmospheres (ATM) of pressure. The stent easily continued to expand, causing the pressure to drop. The inflation was continued until the pressure of 2 ATM was maintained. The stent was then inflated at 1 ATM intervals and the diameters at those pressures once pressure equilibrated were recorded. Inflation was continued until 7 atmospheres was achieved, which was 1 ATM below the rated burst pressure of the balloon. The tube diameter was recorded at each 1 ATM interval using a laser micrometer (LaserMike™ Dayton Ohio).

A similar procedure should be followed for different sizes of tubes and covered stents. For other tube and covered stent sizes, an appropriately sized balloon is chosen. Continue inflating until reaching 1 ATM below the rated burst pressure of the balloon.

Axial Elongation Test

The axial elongation test is performed by elongating a sample in a tensile testing machine at a constant crosshead speed. The gage length of the sample and the crosshead speed are recorded. The intent of the test is to determine the stop point of a sample, should one exist.

The load-extension curves relating to composite materials and covered stents and tubes of the present invention exhibit an inflection point due to the change in slope upon reaching a length referred to as the stop point. An estimate of the stop point is determined in the following manner. The slope of the load-extension curve prior to reaching the stop point can be approximated by drawing a straight line tangent to the curve. The slope of the bad-extension curve beyond the stop point can be approximated by drawing a straight line tangent to the curve. An estimate of the stop point is the extension corresponding to the intersection of the two straight lines.

EXAMPLES

Example 1

An elastomeric composite material was made in the following manner.

Precursor Membrane

A biaxially expanded ePTFE membrane that had not been amorphously locked and had the following properties was obtained: thickness=0.0023 mm, density=0.958 g/cc, matrix tensile strength in the strongest direction=433 MPa, matrix tensile strength in the direction orthogonal to the strongest direction=340 MPa, elongation at maximum load in the strongest direction=39%, and elongation at maximum load in the direction orthogonal to the strongest direction=73%. Upon tensioning by hand, the membrane did not noticeably retract upon the release of the tension.

Retracted Membrane

A roll of precursor membrane where the length direction corresponded with the weakest direction of the membrane was restrained in the clamps of a heated, uniaxial tenter frame and fed into the heated chamber of the tenter frame. The oven temperature was set to about 270° C. The rails of the tenter frame within the heated chamber were angled inward in order to allow membrane shrinkage to about 39% of its original width in response to the heat. The line speed was set to provide a dwell time of about 1.5 minutes within the heated chamber.

The initial and final widths of the membrane were 1625 mm and 632 mm, respectively. The retracted membrane had the following properties: thickness=0.003 mm, density=1.36 g/cc, matrix tensile strength in the strongest direction of the precursor membrane=158 MPa, matrix tensile strength in the direction orthogonal to the strongest direction of the precursor membrane=409 MPa, elongation at maximum load in strongest direction of the precursor membrane=301%, and elongation at maximum load in the direction orthogonal to the strongest direction of the precursor membrane=85%.

Extruded Elastomer

A copolymer comprising tetrafluoroethylene (TFE) and perfluoro(methyl vinylether) (PMVE) as described in U.S. Pat. No. 7,049,380 to Chang, et al. was obtained with a PMVE/TFE ratio of 2:1. The copolymer was extruded at about 350° C. into a thin film. The film had the following properties: thickness=0.025 mm and width=115 mm.

Elastomeric Composite Material

Figure 2A:
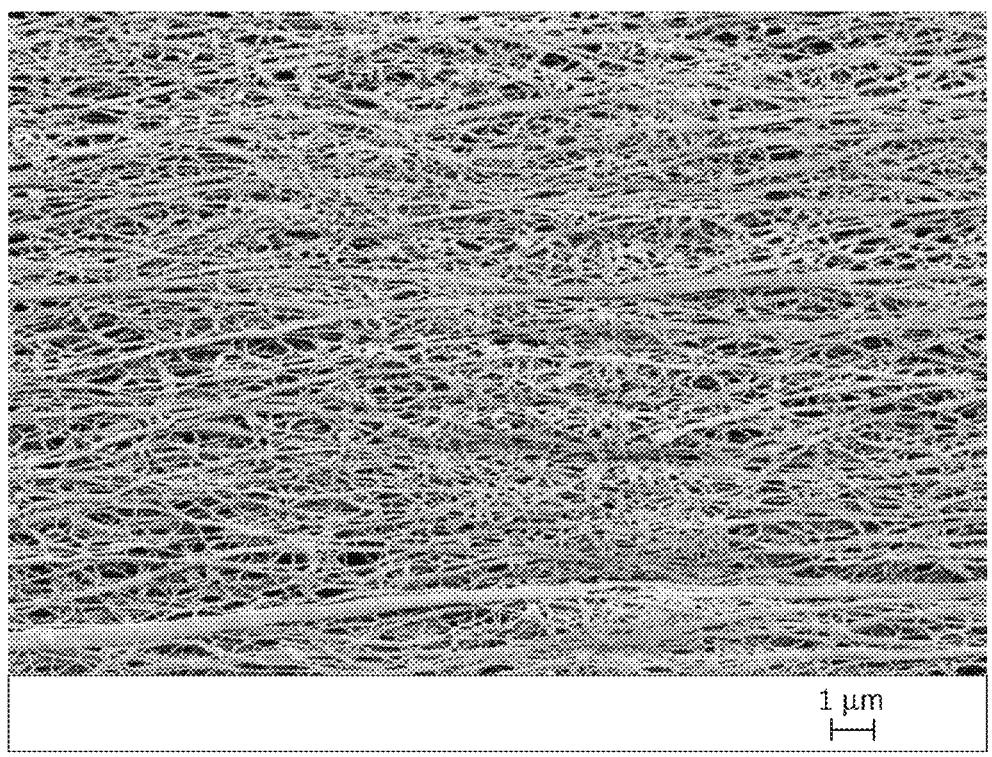
FIG. 2a is a scanning electron micrograph of the surface of an inventive elastomeric composite material taken at 5000×.
Figure 2B:
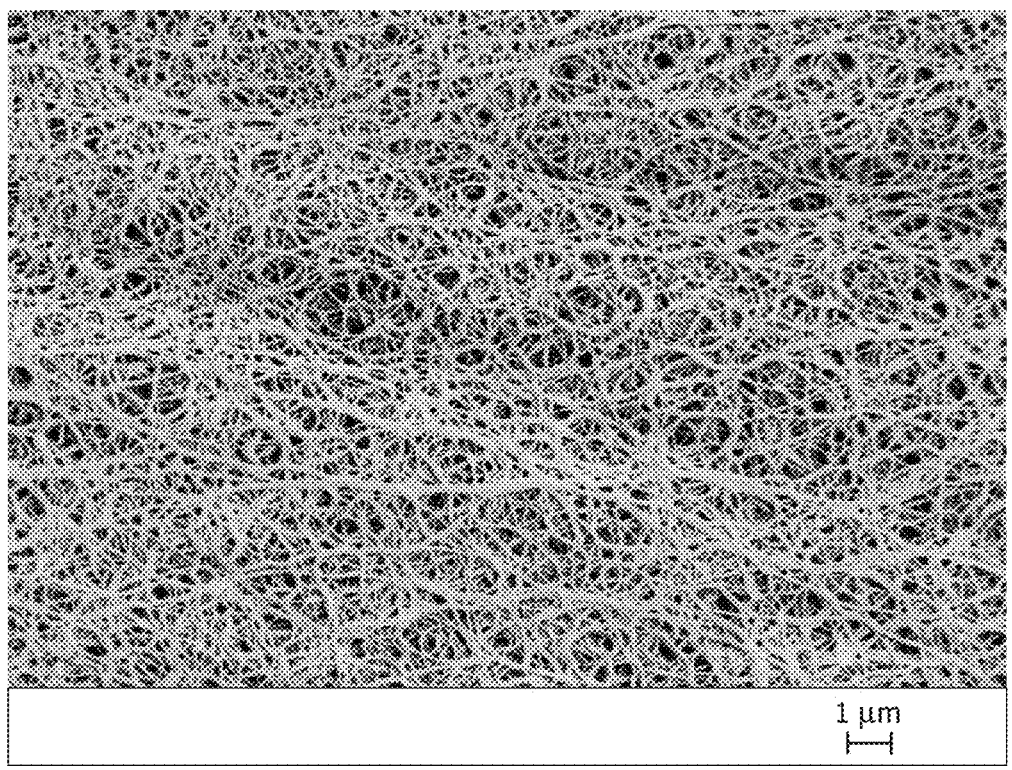
FIG. 2b is a scanning electron micrograph of the surface of the inventive elastomeric composite material of FIG. 2a taken at 5000× after subsequent elongation.

The extruded elastomer was fed onto the surface of the retracted membrane and spooled with a 0.064 mm thick high density polyethylene release film. The elastomeric composite material had the following properties: thickness=0.033 mm and width=115 mm. The elastomeric composite material is shown in FIG. 2a, a SEM of the surface of the membrane opposing the extruded elastomer, taken at 5,000× magnification. A length of the elastomeric composite material was stretched by hand to about 78% of the original length. The fibrils were seen to have a serpentine shape as indicated in FIG. 2b, a SEM of the surface of the membrane opposing the extruded elastomer, taken at 5,000× magnification.

Example 2

A circumferentially covered stent was constructed in the following manner. Nitinol wire (600315-18, Fort Wayne Metals, Fort Wayne, Ind.) was obtained and formed into a stent by winding the wire onto a winding mandrel with appropriately located pins. The stent was 10 cm long and 10 mm in diameter. An ePTFE-fluoropolymer elastomeric composite material as described in detail above which had the following properties: film thickness=0.006 mm elastomer thickness=0.025 mm was obtained. A liquid solution of PAVE-TFE, as described previously, and Fluoroinert® (3M Fluoroinert, 3M Specialty Chemicals Division, St. Paul, Minn.) was obtained and combined to form a solution. The stent was removed from the winding mandrel and dipped into the solution. The stent was air dried then placed onto a 10 mm mandrel that had a covering of Kapton film (Lot #B4N0C38500ADD, E. I. du Pont de Nemours and Company, Wilmington, Del.). One end of the mandrel was secured inside the chuck of a drill. The elastomeric composite material was cut to about 100 mm in width. It was noted that the length direction of the composite material was the direction that possessed the elastomeric properties.

Figure 4:
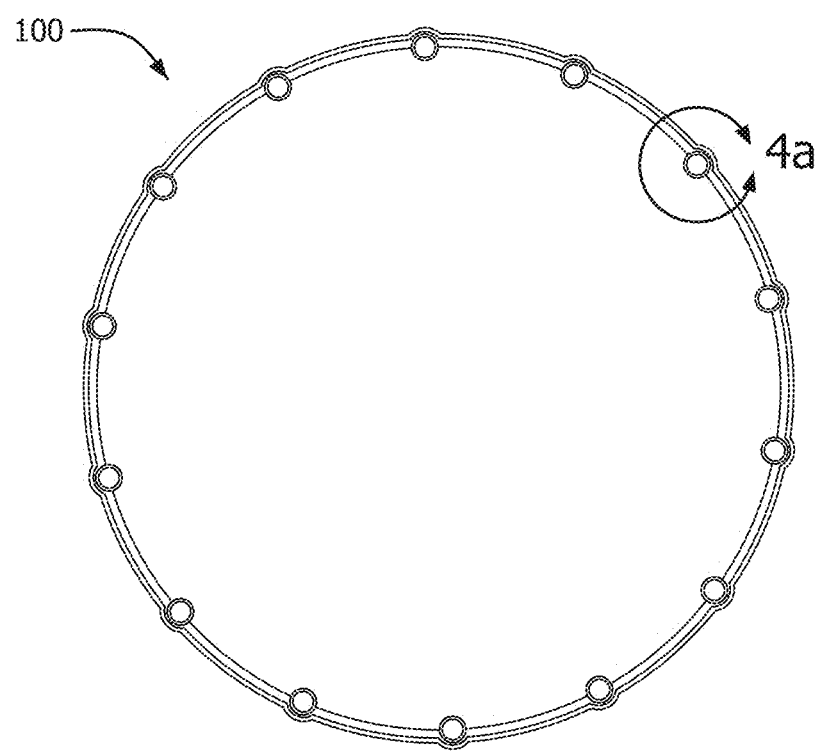
FIG. 4 is a schematic illustration of an exemplary elastic stent graft according to the instant invention.
Figure 4A:
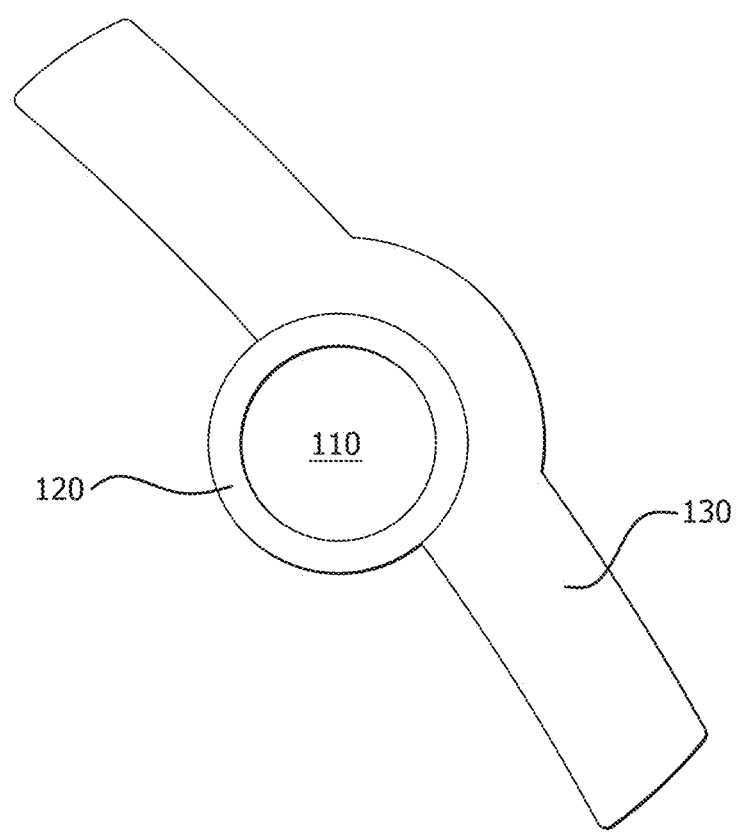
FIG. 4a is a schematic illustration depicting a portion of the elastic stent graft of FIG. 4 showing a wire coated with an adhesive and the circumferentially applied composite material.

With the drill secured, the composite material was circumferentially applied to the stent such that the elastic direction of the material was tangent to the axial direction of the stent. The elastomer side of the composite material was applied to the stent with pressure and was secured to the stent under tension due to the tackiness of the elastomer. Tension was applied to the composite material to elongate it. The amount of tension was sufficient to exceed the retraction force without disrupting the material but lower than the stop point. The drill rotated the mandrel until one composite material layer was wrapped onto the stent. A compression wrap was applied to the covered stent in the following manner. A layer of Kapton film was applied, followed by the application of an ePTFE film applied under tension to ensure uniform contact between the composite material and the stent. The assembly was placed in an oven set to about 50° C., for about 24 hours. The stent plus films was removed from the mandrel and the outer ePTFE film and Kapton films were removed, thereby resulting in a covered stent. FIG. 4 is a schematic illustration of a cross-sectional view of an exemplary elastic stent graft 100 according to the instant invention. FIG. 4a, schematically depicts the wire 110 coated with an adhesive 120 and the composite material 130 circumferentially applied to the stent.

When the covered stent was crushed from 10 mm to 8 mm by pulling it through a funnel, no folds in the stent cover were observed.

Example 3

An axially covered stent was made as described in Example 2 with the following exceptions. The composite material was applied such that the direction of the film possessing the elastomeric properties was in the axial direction of the stent.

Figure 3:
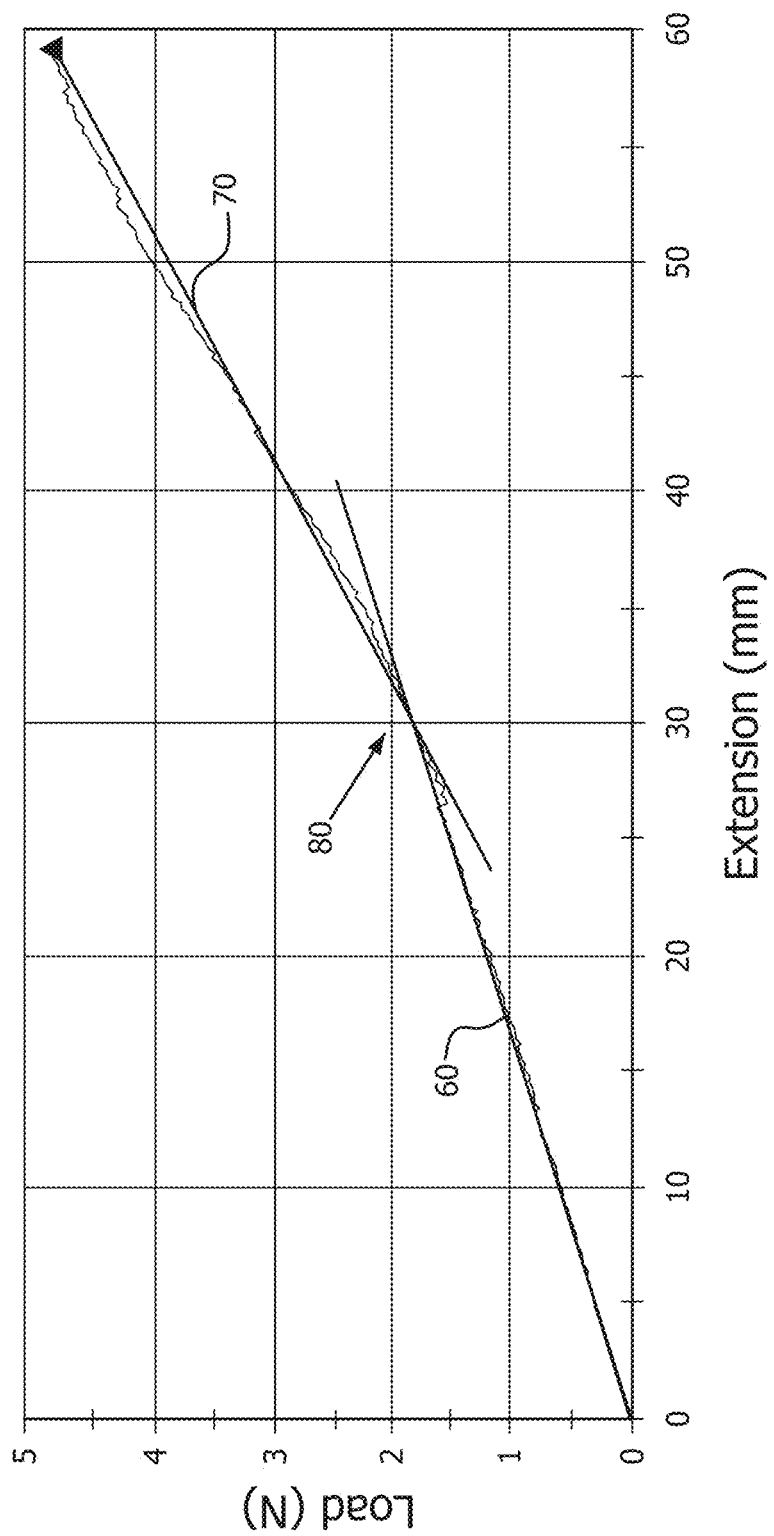
FIG. 3 is a load versus extension curve corresponding to an axially wrapped stent according to the present invention.

The axial elongation test performed with a gage length of 82.5 mm and a crosshead speed of 60 mm/min demonstrated that the stent graft axially elongated and incorporated a stop point at about 30 mm. FIG. 3 is a load vs. extension curve corresponding to the axially wrapped stent showing the stop point 80 at about 30 mm, where tangent lines 60, 70 intersect. The stent graft recovered to approximately its original length upon removal of the tensile force without substantial wrinkling.

Example 4

An axially wrapped tube was made in accordance with the process described in Example 2 with the following exceptions. A tube was constructed without involving a stent. The axial elongation test described above demonstrated that the tube axially elongated and incorporated a stop point. The tube recovered to approximately its original length upon removal of the tensile force.

Example 5

A helically wrapped tube was made in accordance with the process described as follows. An ePTFE-fluoropolymer composite material as described in Example 1 was obtained having the following properties: film thickness=0.006 mm, elastomer thickness=0.025 mm. The composite material was slit to about 100 mm wide. A helically wrapped tube was made by first wrapping a Kapton film covering ((Lot #B4N0C38500, E. I. du Pont de Nemours and Company, Wilmington, Del.)) over a 10 mm stainless steel mandrel and then wrapping one layer of the composite material, with the elastomer side facing outward, on top of the Kapton film at an angle of approximately 45 degrees relative to the longitudinal axis of the mandrel. Then, another layer of the composite material was wrapped over the first layer of composite material, but with the elastomer layer facing inward and at an angle 90 degrees relative to the first composite material. In this way, the helically wrapped tube had two layers of composite material, one layer at 45 degrees relative to the longitudinal axis and another layer at 135 degrees relative to the longitudinal axis.

A compression wrap was applied to the outer layer in the following manner. A layer of Kapton film was helically wrapped over the outermost composite material, followed by an ePTFE film applied under tension to ensure uniform contact between the composite film layers. The resulting assembly was placed in an oven set to 50° C. for approximately 24 hours to bond the two layers of the composite material to each other. The coverings and helically wrapped tube were removed from the mandrel and the coverings were removed from the tube. The resulting helically wrapped tube was 10 cm long and 10 mm in diameter.

The axial elongation test performed with a gage length of 82.5 mm and a crosshead speed of 10 mm/min demonstrated that the tube axially elongated and incorporated a stop point at about 12 mm. The tube recovered to approximately its original length upon removal of the tensile force.

FIG. 6 is a pressure vs. diameter curve corresponding to the helically wrapped tube. The pressure vs. diameter test described above demonstrated that the tube had a stop point at about 14 mm. The tube recovered to approximately its original diameter upon removal of the internal pressure.

Figure 5:
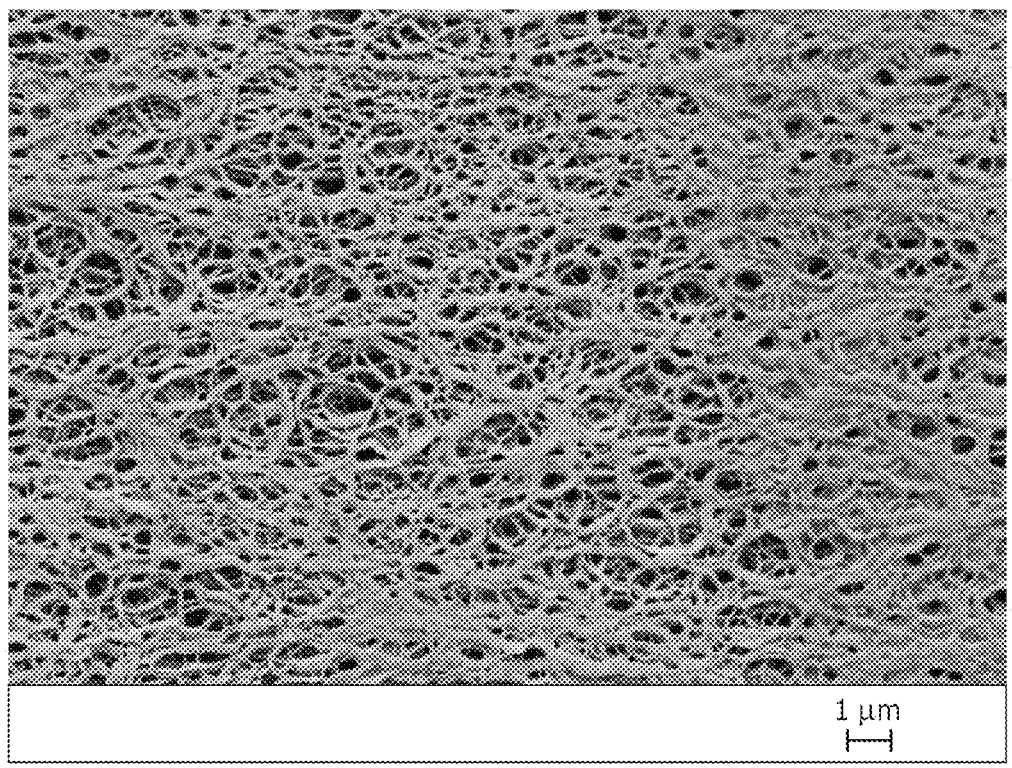
FIG. 5 is a scanning electron micrograph of the surface of a helically wrapped tube with the copolymer partially removed taken at 5000×.

The fibrils of the membrane were noted to have a serpentine shape as shown in FIG. 5, a scanning electron micrograph of the surface of helically wrapped tube with the copolymer partially removed taken at 5000×.

The invention of this application has been described above both generically and with regard to specific embodiments. The invention is not otherwise limited, except for the recitation of the claims set forth below.

What is claimed is:

1. A stent graft having a compacted diameter and being received on a delivery device at the compacted diameter, the stent graft having a nominal diameter to which the stent-graft tends to self-expand from the compacted diameter upon deployment from the delivery device, the stent graft comprising:
    a stent having a wall with at least one opening, an outer surface, and an inner surface; and
    a cover affixed to said stent, the cover comprising a composite material comprising at least one expanded fluoropolymer membrane and an elastomer, the expanded fluoropolymer membrane comprising a plurality of serpentine fibrils such that the composite material of the cover is configured to cause the cover to be wrinkle-free at a first diameter corresponding to the compacted diameter and wrinkle-free at a second diameter that is larger than the first diameter and which corresponds to the nominal diameter to which the stent-graft tends to self expand, and further wherein the composite material of the cover is configured to cause the cover to be elastically expandable beyond the nominal diameter and to have a stop point at a diameter greater than the nominal diameter at which the composite material exhibits a sharp increase in stiffness.

2. The stent graft of claim 1, wherein each said serpentine fibril has a width of about 1.0 micron or less.

3. The stent graft of claim 2, wherein each said serpentine fibril has a width of 0.5 micron or less.

4. The stent graft of claim 1, wherein said cover is affixed to said outer surface.

5. The stent graft of claim 1, wherein said cover is affixed to said inner surface.

6. The stent graft of claim 1, wherein said cover is affixed to said outer surface and said inner surface.

7. The stent graft of claim 1, wherein said elastomer is present in pores of said fluoropolymer membrane.

8. The stent graft of claim 1, wherein said at least one expanded fluoropolymer membrane comprises a plurality of pores and said elastomer is present in substantially all of said pores.

9. The stent graft of claim 1, wherein the fluoropolymer membrane comprises polytetrafluoroethylene.

10. The stent graft of claim 1, wherein the fluoropolymer membrane comprises a microstructure of substantially only fibrils.

11. The stent graft of claim 1, wherein the fluoropolymer membrane comprises a plurality of serpentine fibrils.

12. The stent graft of claim 1, wherein the expanded fluoropolymer membrane comprises a microstructure of substantially only serpentine fibrils.

13. The stent graft of claim 1, wherein said composite material can be radially expanded up to a diameter beyond which further expansion is inhibited.

14. The stent graft of claim 1, wherein said cover is wrinkle free when radially expanded to about 90% of a nominal diameter.

15. The stent graft of claim 1, wherein said cover is wrinkle free when radially expanded to about 85% of a nominal diameter.

16. The stent graft of claim 1, wherein said cover is wrinkle-free when radially expanded to about 80% of a nominal diameter.

17. The stent graft of claim 1, wherein said composite material is free of wrinkles before loading and after deployment of said device.

18. The stent graft of claim 1, wherein said composite material is circumferentially wrapped around said stent.

19. The stent graft of claim 1, wherein said composite material is axially wrapped around said stent.

20. The stent graft of claim 1, wherein said composite material is helically wrapped around said stent.

21. The stent graft of claim 1, wherein said composite material is both circumferentially and axially wrapped around said stent.

22. The stent graft of claim 1, wherein the stent comprises a self-expanding stent.

23. The stent graft of claim 1, wherein elastic properties are present in the axial direction of the stent graft.

24. The stent graft of claim 1, wherein said elastomer is selected from the group consisting of perfluoromethylvinyl ether-tetrafluoroethylene copolymers, perfluoro (alkyl vinyl ether)-tetrafluoroethylene copolymers, silicones and polyurethanes.

* * * * *